US00PP34947P3

(12) United States Plant Patent
Olesen

(10) Patent No.: US PP34,947 P3
(45) Date of Patent: Jan. 31, 2023

(54) MINIATURE ROSE PLANT NAMED 'POULPAH108'

(50) Latin Name: *Rosa hybrida*
Varietal Denomination: 'Poulpah108'

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 78 days.

(21) Appl. No.: 17/300,632

(22) Filed: Sep. 7, 2021

(65) Prior Publication Data

US 2022/0104414 P1 Mar. 31, 2022

(30) Foreign Application Priority Data

Sep. 21, 2020 (QZ) ..... PBR 2020/2252

(51) Int. Cl.
*A01H 5/02* (2018.01)
*A01H 6/74* (2018.01)

(52) U.S. Cl.
USPC ..... Plt./118
CPC ..... *A01H 6/749* (2018.05)

(58) Field of Classification Search
USPC ..... Plt./101, 116, 118
See application file for complete search history.

(56) References Cited

PUBLICATIONS

CPVO Register—https://online.plantvarieties.eu/publicSearch; Retrieved from the Internet on Oct. 21, 2021; citation for 'Poulpah108'.*

* cited by examiner

*Primary Examiner* — Susan McCormick Ewoldt

(57) ABSTRACT

A new garden rose plant of the Miniature class which has abundant, deep yellow flowers and attractive foliage. This new and distinct variety has shown to be uniform and stable in the resulting generations from asexual propagation.

2 Drawing Sheets

Botanical designation: *Rosa hybrida.*
Variety denomination: 'Poulpah108'.

This application claims priority to Plant Breeder's Rights Application Number 2020/2252, which was filed at the Community Plant Variety Rights Office in the European Union on Sep. 21, 2020, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2012 and the resulting seeds were planted in a controlled environment in Fredensborg, Denmark. The new variety, named 'Poulpah108', originated as a single seedling from the stated cross.

The new variety may be distinguished from its male pollen parent and female seed parent primarily by the following characteristics. The male pollen parent plant has light yellow flowers while the new variety has deep yellow flowers. The female seed parent plant has apricot flowers while the new variety has deep yellow flowers.

The objective of the hybridization of this rose variety was to create a new and distinct variety with unique qualities, such as:

1. Uniform and abundant deep yellow flowers;
2. Vigorous, but very compact growth when propagated on its own roots;
3. Exceptional disease resistance.

This combination of qualities is not present in previously available commercial cultivars of this type, known to the inventor, and distinguish 'Poulpah108' from all other varieties of which we are aware.

As part of the rose development program, Mogens N. Olesen germinated the seeds from the aforementioned hybridization during winter of 2012 and conducted evaluations on the resulting seedlings in a controlled environment in Fredensborg, Denmark. 'Poulpah108' was selected in the spring of 2013 by the inventor as a single plant from the progeny of the aforementioned hybridization.

Asexual reproduction of 'Poulpah108' by rooted cuttings was first done by Mogens N. Olesen in the nursery in Fredensborg, Denmark in July, 2013. This initial and other subsequent asexual propagations conducted in controlled environments have demonstrated that the characteristics of 'Poulpah108' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah108'.

Specifically illustrated in FIG. 1 of the drawings are flowers at various stages of opening, flower petals detached, sepals detached showing receptacle and pedicel.

Figure 1:
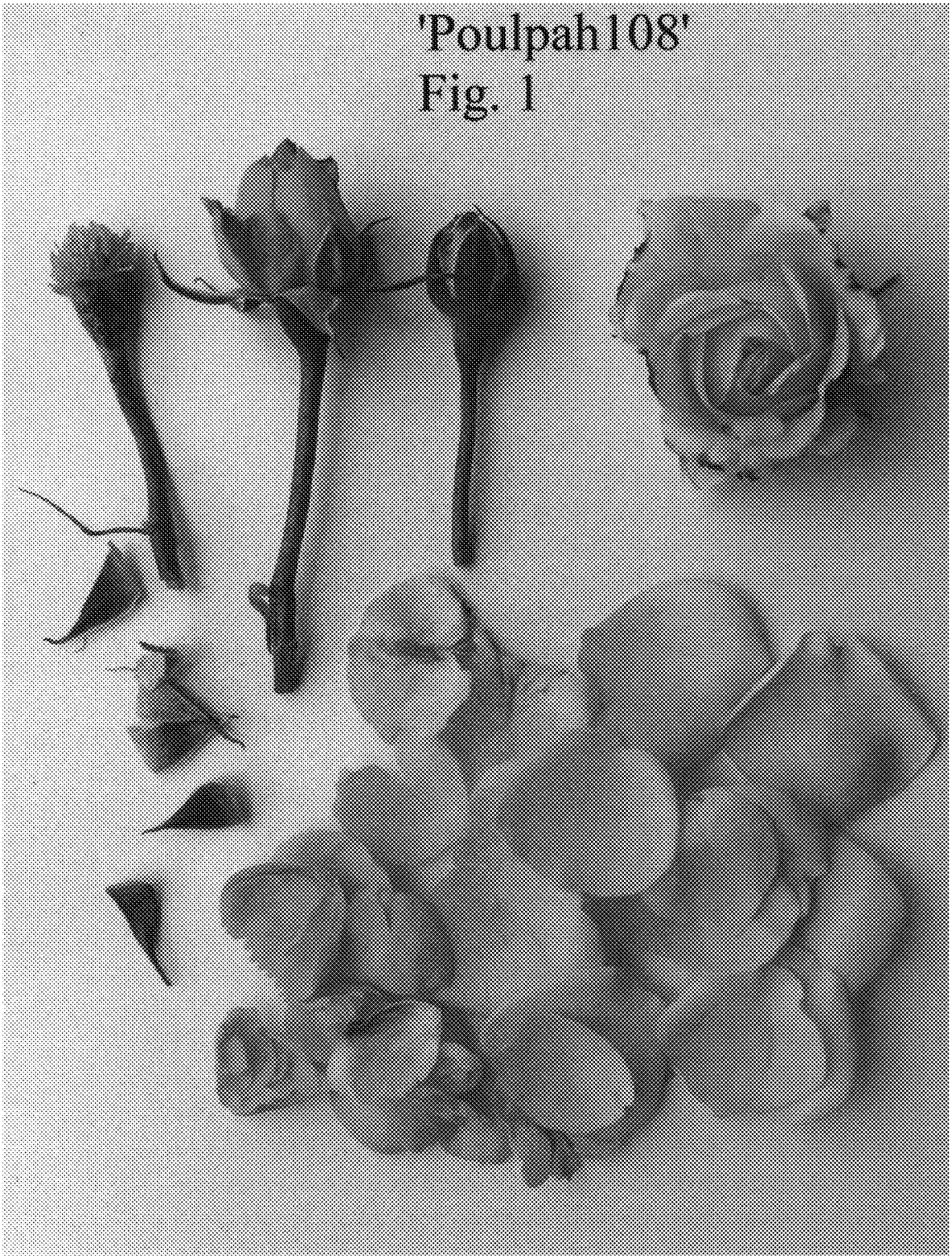
Figure 2:
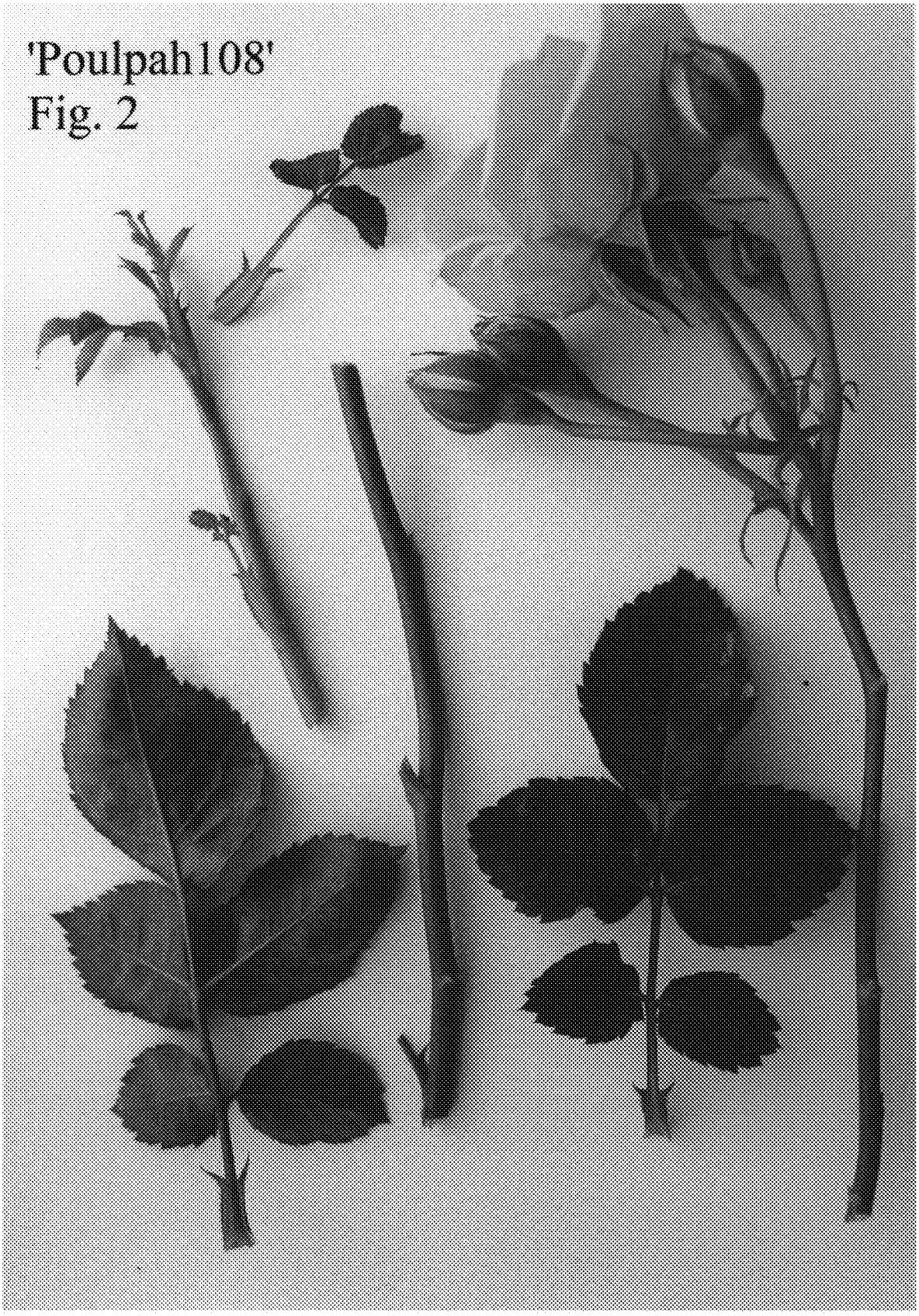

Specifically illustrated in FIG. 2 of the drawings is a cluster of flowers on the branch, juvenile and mature leaves, as well as stems. Plants shown are 1.5 years of age.

DETAILED DESCRIPTION OF THE VARIETY

The following is a description of 'Poulpah108', as observed in its growth in a field nursery in Linn County, Oreg. Observed plants are 1.5 years of age, and were grown on their own roots. Color references are made using The Royal Horticultural Society (London, England) Colour Chart, 2001, except where common terms of color are used.

For a comparison, several physical characteristics of the rose variety 'Poulpah088', U.S. Plant Pat. No. 29,717 are compared to 'Poulpah108' in Chart 1.

CHART 1

| | 'Poulpah108' | 'Poulpah088' |
|---|---|---|
| Petal Count | 45 | 70 |
| Flower Diameter | 55 mm | 90 |
| General Tonality of Flower Color | Yellow Group 13A & 13B | Yellow Group 10A |

FLOWER AND FLOWER BUD

Blooming habit: Continuous.

Flower bud:

*Size*.—Upon opening, 26 mm in length from base of receptacle to end of bud. Bud diameter is 14 mm.

*Bud form*.—Urceolate.

*Bud color*.—As sepals divide petals are Red Group 53B and Yellow Group 8B.

*Sepal inner surface*.—Color: Yellow-Green Group 147C with intonations of Greyed-Red Group 180C. Surface: Lightly pubescent.

*Sepal outer surface*.—Color: Yellow-Green Group 144A with intonations of Greyed-Red Group 180B. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—24 mm long, 7 mm wide.

*Receptacle*.—Texture: Smooth. Size: 8 mm in height, 7 mm wide. Color: Yellow-Green Group 144A with intonations of Greyed-Red Group 180B. Shape: Funnel.

*Pedicel*.—Surface: Smooth. Length: 40 mm. Diameter: 2 to 3 mm average. Color: Yellow-Green Group 144B and Greyed-Red Group 180B. Strength: Strong.

*Peduncle*.—Length: 1 to 3 cm. Diameter: About 4 mm. Color: Yellow-Green Group 144A. Texture: Smooth.

Flower bud development: Flower buds are borne in clusters of 5 to 7 flower buds per stem. Development as a panicle.

Flower bloom:

*Fragrance*.—None.

*Duration*.—The blooms have a duration on the plant of approximately 18 days. Petals fall cleanly away from plant after flowers have fully matured.

*Size*.—Flower diameter is 55 mm when open. Flower depth is 24 mm.

*Flower shape*.—Cupped.

*Shape of flower, side view*.—The upper portion is flat. The lower portion is concave.

Petalage: Under normal conditions, flowers have about 45 petals.

General tonality of flower: Open flowers are Yellow Group 13A & 13B.

Petal color:

*Outer petals*.—Upper surface: Yellow Group 9A at the basal zone. At middle zone Yellow Group 12A, and Yellow Group 12B at the marginal zone. Lower surface: Yellow Group 13A. At the basal zone Yellow Group 7A. Intonations of Greyed-Purple Group 184C and Yellow-Green Group 145C on the guard petals.

*Inner petals*.—Upper surface: Yellow Group 9A at the basal zone. At middle zone Yellow Group 12A, and Yellow Group 12B at the marginal zone. Lower surface: Yellow Group 13A. At the basal zone Yellow Group 7A. Shaded with Yellow-Orange Group 22A.

Petals:

*Petal reflex*.—Somewhat reflexed at the margin.

*Margin*.—Entire and uniform. No undulations.

*Shape*.—Broad and elliptic. Apex shape: Rounded. Base shape: Obtuse.

*Size*.—30 mm (l)×31 mm (w).

*Texture*.—Smooth.

*Thickness*.—Average.

Petaloids:

*Size*.—10 mm (l) by 10 mm (w).

*Quantity*.—8 to 10.

*Shape*.—Elliptical and rounded. The apex is rounded, with strong undulations of the margin. The base is acute and rounded.

*Color*.—The upper side is Yellow Group 9A at the basal zone and Yellow Group 12A at middle and marginal zone. Yellow Group 13A on the lower surface shaded with Yellow-Orange Group 22A.

Reproductive flower parts:

*Pollen*.—None observed.

*Anthers*.—Size: 2 mm in length. Color: Yellow Group 8C. Quantity: 40 on average.

*Filaments*.—Color: Yellow Group 13A. Length: 3 mm.

*Pistils*.—Length: 9 mm. Quantity: 25 on average.

*Stigmas*.—Color: Greyed-Yellow Group 160C.

*Styles*.—Color: Greyed-Yellow Group 160C.

*Location of stigmas*.—Superior in location relative to the length of the filaments and the height of the anthers.

*Hips*.—None Observed.

PLANT

Plant growth: Very compact, upright, and well branched. Plants are 25 cm in height, and 29 cm wide.

Stems:

*Color of juvenile growth*.—Yellow-Green Group 146C.

*Color of mature growth*.—Yellow-Green Group 146B with light intonations of Greyed-Orange Group 175D.

*Length*.—Canes are about 13 cm from the base of the plant to the flowering portion.

*Diameter*.—About 4 mm.

*Internodes*.—On mature canes about 28 mm between nodes.

*Surface texture*.—Young wood: Smooth. Older wood: Smooth.

Long prickles: None observed.

Plant foliage:

*Compound leaf*.—About 120 mm (l)×75 (w).

*Quantity*.—3 leaves per 10 cm of stem on average.

*Leaf bearing angle to the stem*.—45 degrees.

*Color of juvenile foliage*.—Upper side: Yellow-Green Group 144A with anthocyanin the color of Greyed-Red Group 168B shaded and at the margins. Lower side: Yellow-Green Group 144A shaded with Greyed-Red Group 168B.

*Color of mature foliage*.—Upper side: Yellow-Green Group 147A. Lower side: Yellow-Green Group 147B.

Plant leaves and leaflets:

*Stipules*.—Size: 15 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 25 mm. Diameter: 2 mm. Upper surface color: Yellow-Green Group 144A. Lower surface color: Yellow-Green Group 144A.

*Rachis*.—Length: 41 mm. Upper surface color: Yellow-Green Group 144A. Lower surface color: Yellow-Green Group 144A.

*Leaflet*.—Quantity: Normally 5 leaflets. Margins: Double serrated. Size: Terminal leaflets are about 54 mm long, 44 mm wide. Shape: Generally elliptical. Base: Rounded. Apex: Acute. Texture: Smooth. Thickness: Average. Arrangement: Odd pinnate. Venation: Reticulate. Glossiness: Glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpah108', substantially as illustrated and described herein, due to its abundant deep yellow flowers, disease resistance, and extended period of bloom.

* * * * *

'Poulpah108'

'Poulpah108'